United States Patent [19]

Hall et al.

[11] Patent Number: 4,527,435

[45] Date of Patent: Jul. 9, 1985

[54] CHANNELED PLUG PROPORTIONAL FLOW SAMPLER

[75] Inventors: Kenneth R. Hall, College Station; James C. Holste, Bryan, both of Tex.

[73] Assignee: Precision Machine Products, Inc., Dallas, Tex.

[21] Appl. No.: 553,370

[22] Filed: Nov., 1983

[51] Int. Cl.³ .............................................. G01N 1/22
[52] U.S. Cl. ............................ 73/863.03; 73/863.61
[58] Field of Search ................. 73/863.61, 863.03, 202

[56] References Cited

U.S. PATENT DOCUMENTS

| | | | |
|---|---|---|---|
| 3,377,867 | 4/1968 | Nitescu | 73/863.61 |
| 3,478,600 | 11/1969 | Lynn | 73/863.03 |
| 3,559,482 | 2/1971 | Baker et al. | 73/202 |
| 3,777,562 | 12/1973 | Clingman, Jr. | 374/112 |
| 3,930,414 | 1/1976 | Russel | 73/863.03 |
| 4,062,236 | 12/1977 | Clingman, Jr. | 374/112 |
| 4,080,831 | 3/1978 | Roberts et al. | 73/863.61 |
| 4,125,018 | 11/1978 | Clingman, Jr. | 374/116 |
| 4,125,123 | 11/1978 | Clingman, Jr. | 374/37 |
| 4,246,788 | 1/1981 | Olin et al. | 73/863.03 |
| 4,396,299 | 8/1983 | Clingman, Jr. et al. | 374/37 |
| 4,446,748 | 5/1984 | Clingman et al. | 73/863.61 |

*Primary Examiner*—Tim Miles

*Attorney, Agent, or Firm*—Stanley R. Moore; Thomas L. Cantrell

[57] ABSTRACT

An improved proportional gas flow sampler having a combined arrangement of channeled plugs in a main flow line and a sample flow line for obtaining proportionally constant flow samples. The channels in the main line plug have relatively equivalent hydraulic diameters and a substantially greater average cross-sectional area than the channels in the sample line plug. The hydraulic diameter of the sample line plug channels are, however, within an order of magnitude of the hydraulic diameter of the main line plug channels and in certain configurations, relatively equivalent. The pressure drop across the main line and sample line plugs is held constant to impose an equivalent flow impedance, even with proportionally greater flow through the main line plug. In this manner, the arrangement extracts a fixed fraction of the flow into the sample line regardless of overall flow rate. Downstream of the plugs, a control valve is disposed which is responsive to a differential pressure transducer to provide the equal pressure drop as the sample flow is extracted. The sample flow rate typically is a very small percentage of the flow in the main line which, in the present invention, is independent of the relative cross-sectional areas of the channels in the plugs. An advantageously high split is therefore possible in a manner independent of flow rate.

17 Claims, 3 Drawing Figures

CHANNELED PLUG PROPORTIONAL FLOW SAMPLER

BACKGROUND OF THE INVENTION

1. Field of the Invention

This invention relates to flow sampling systems and, more particularly, to proportional gas flow sampling method and apparatus utilizing a channeled flow splitting device.

2. History of the Prior Art

The prior art is replete with systems adapted for taking proportionally constant samples from flowing gas streams in gas lines. The purposes of such samples is to make measurements of various types representative of the main gas flow. Proportionality of the sample is important in order to avoid variable calibration factors, and the challenge is to provide equipment which takes a proportionally constant sample over an appreciable range of flow rates in the main gas line. The methods and apparatus set forth and described in U.S. patent application Ser. No. 06/272,204 filed June 10, 1981, now U.S. Pat. No. 4,396,299, and assigned to the assignee of the present application sets forth one embodiment of such a device. While the present invention is useful in other applications as well, the equipment disclosed in said patent application forms a good illustration of flow measurement systems.

Other prior art systems have specifically addressed the division of flow for constant proportionality measurement. For example, co-pending U.S. patent application Ser. No. 06/325,312 filed Nov. 22, 1981, now U.S. Pat. No. 4,446,748, teaches such a system wherein a baffle arrangement is provided in a main gas flow line such that a constant proportion of the total flow enters a by-pass line upon diversion by the baffle. It is known in the prior art to use just baffles for proportional flow sampling, at least over a narrow range of flow rates. A sampler relying solely on baffles has a very simple piping arrangement, and an advantage of the baffle system is that little pressure drop is introduced into the main line. A disadvantage of the baffles is that the proportional cut should not be less than 10–20% of the total flow. If one tries to extract too small a fraction, then changes in the flow profile as a function of Reynolds number will have a significant effect and reduce accuracy. Other prior art systems incorporate a sampler relying solely upon an orifice arrangement without baffles. Such an arrangement is disclosed in the above-mentioned patent application Ser. No. 06/272,204. An advantage of the orifice sampling system is that a very small cut can be taken from the main line, such as one part in one thousand.

A disadvantage of either a baffle system or an orifice plate system by themselves is that the dynamic range is limited in an energy flow meter application. In the latter instrument, a proportional flow sampler is combined with a modified titrator-type apparatus for determining energy content or calorific value of the kind generally disclosed in U.S. Pat. Nos. 3,777,562 issued Dec. 11, 1973; 4,062,236 issued Dec. 13, 1977; 4,125,018 issued Nov. 14, 1978; and 4,125,123 also issued Nov. 14, 1978. In the energy meter section of such equipment, the sample flow is mixed with air and burned. There will only be about a five-to-one range of flows that can be accommodated with a single burner design and the greater the flow range at the burner, the less the inherent accuracy will be.

Other prior art approaches to proportional flow sampling have addressed the critical aspect of obtaining representative samples through flow division and pressure regulation. For example, U.S. Pat. No. 3,377,867 to Nitescu sets forth an automatic sampling device comprising a flow divider and pressure stabilizing means for equalizing the flow within the channels of the flow divider. This conventionally accepted method of flow division affords automatic sampling for a multiphase, non-homogenous fluid. The flow division principle incorporates an orifice plate and channel block having a plurality of channels of identical dimension for permitting flow therethrough. The flow through one channel is, however, fed to a by-pass line through a direct tap coupling, and the flow therethrough is regulated by a zero differential flow controller. The flow controller nullifies any pressure differential between the valve and the exit whereby flow through the by-pass line will be identical to the flows through the other channels. Such differential flow regulation is an integral part to proper flow sampling and is particularly critical to sampling units of the type described above utilizing an isolated section of diverted flow. Disadvantages of such methods and apparatus include the inherent limitations to the possible flow splits for sampling. The division of flow is obviously directly related to the number of identical channels through which flow is permitted to pass. The availability of high split ratios is therefore limited in such systems to the number of channels which can be provided. This limitation can become critical in instances of ordinary flow variation.

Another prior art approach is shown in U.S. Pat. No. 3,930,414 to Russel wherein a variable flow restriction in the sample line is provided to maintain proportionality to the pressure drop across a flow restricter in the main line. Certain advantages exist for such proportional flow sampling systems. The variable flow restriction system has been shown to be effective in establishing flow regulation without the use of sectioned flow dividing units. Such systems utilize main line orifice plate assemblies and differential pressure sensors thereacross for establishing flow proportionality. Certain disadvantages remain, however, relative to flow sampling ratios and accurate proportionality during flow rate variations without the utilization of a flow divider.

It would be an advantage, therefore, to incorporate certain ones of the advantages of a flow dividing unit with an upstream sampling unit whereby a proportional flow sample may be obtained with maximum efficiency and accuracy and a minimum of complex hardware coupled thereto. The methods and apparatus of the present invention provide such a system by incorporating channeled plugs in the main flow line and an upstream sample line for obtaining proportional flow sampling. The system is also constructed wherein the average cross-sectional area per channel in the main line plug is substantially greater than the average cross-sectional area per channel in the sample line plug, while the hydraulic diameters of each are relatively equivalent, or within pre-defined ranges. In this manner, a fixed fraction of the flow into the sample line is maintained regardless of overall flow rates and wherein an advantageously high split is possible without the necessity of a plug having an equal number of apertures corresponding to the flow split ratio.

SUMMARY OF THE INVENTION

The present invention relates to an improved system for taking a proportionally constant flowing sample from a gas stream flowing through a main gas flow line at rates subject to variation. More particularly, one aspect of the system includes a channeled plug flow divider mounted in the main gas line. A channeled plug is also disposed in a sample line which extends out of the main gas line upstream of the channeled plug flow divider. The average cross-sectional area per channel of the main line plug is substantially greater than the average cross-sectional area per channel in the sample line plug. The hydraulic diameters of the channels of the main line plug are relatively equivalent as are the hydraulic diameters of the channels of the sample line plug. Moreover, the hydraulic diameters of the channels of the sample line plug are within the same order of magnitude as those of the main line plug. In this manner, a greater area for flow is provided in the channels of the main line plug than in the sample line plug resulting in high split ratio and insignificant changes in the proportional split for gross changes in flow rates.

In another aspect, the invention includes the channeled plug flow sampling system set forth above, wherein a second stage flow splitting and sampling system is provided downstream of the first sample line for receiving flow therefrom and providing a secondary flow split. The second stage flow splitting system comprises first and second flow lines coupled in parallel flow relationship to the sample line. A third channeled plug flow splitter mounted within the first flow line is formed with a plurality of channels extending therethrough having relatively equivalent hydraulic diameters. A fourth channeled plug mounted within the sample line has at least one channel formed therein for the passage of gas therethrough having an hydraulic diameter within the same order of magnitude as the hydraulic diameter of the channels of the third channeled plug. The channels of the third plug are also formed with an average cross-sectional area substantially greater than the cross-sectional area of the channel of the fourth plug. Means may also be provided for detecting the magnitude of the pressure drop across the third and fourth plugs in conjunction with means for altering the pressure and flow conditions across the fourth plug. In this manner, the system will selectively match the pressures obtained across the third plug to thereby establish flow through the second flow line at a constant proportion of the flow through the first flow line.

In yet another aspect, the invention includes a method of taking a flowing sample of gas flowing through a line, which flowing sample is constantly proportionate to the flow rate of the flowing gas. The method comprises providing a first channeled plug flow splitter mounted within the line and being formed with a plurality of channels extending therethrough having relatively equivalent hydraulic diameters. Gas is passed through the line through the first plug. A flowing sample of the gas is then drawn from the line at a point upstream of the first plug into a sample line. A second channel plug is mounted within the sample line having at least one channel formed therein for the passage of gas therethrough. The second plug has an hydraulic diameter within the same order of magnitude as the hydraulic diameter of the channels of the first channel plug. Moreover, the channels of the first plug are formed with an average cross-sectional area substantially greater than the cross-sectional area of the channels of the second plug. Gas is then passed in the sample line through the second channel plug mounted in the sample line. The downstream pressure may also be equalized across the first and second plugs by detecting the difference between the pressures and operating a valve in the sample line in a direction to eliminate the difference. The method may further include the step of providing the first plug with channels having hydraulic diameters within ten percent of one another. The method may also include providing the first plug with generally rectangular channels and the second plug with at least one generally cylindrical channel wherein the cylindrical channels have a diameter substantially equal to twice the value of the product of the first plug rectangular channel length times channel width divided by the sum of the length and width.

BRIEF DESCRIPTION OF THE DRAWINGS

For a more complete understanding of the present invention and for further objects and advantages thereof, reference may now be had to the following description taken in conjunction with the accompanying drawing in which.

DESCRIPTION OF THE PREFERRED EMBODIMENTS

Figure 1:
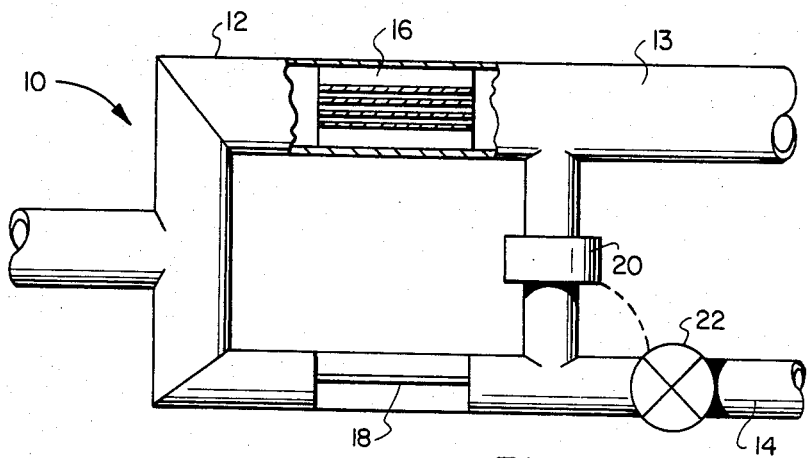
FIG. 1 is a diagrammatic, side-elevational view, with parts partly broken away, of a preferred embodiment of a flow sampler constructed in accordance with the present invention.

Referring first to FIG. 1, there is shown a gas flow system 10 incorporating the flow sampling method and apparatus of the present invention. The system 10 is constructed for measurement of energy flow in a gas pipeline comprising a main line 12 and sample line 14. A flow splitting device 16 is disposed within the main line 12 for imparting a controlled flow through a channeled plug 18 disposed within the sample line 14. The flow splitting configuration of the present invention affords controlled flow in pre-selected high split proportions substantially independent of the Reynolds number of the flow in the main stream and variations in flow rates therethrough. Such a system 10 may permit a determination of the energy flow in the main line in a much more precise and economically feasible manner than heretofore available.

Still referring to FIG. 1, the plug 16 disposed within the main line 12 comprises a channeled member, the present embodiment of which includes a plurality of slots and apertures formed therethrough. The configuration of the plug 16 in conjunction with the methods and apparatus of the present invention affords accurate flow measurement. The accuracy of the flow measurements has been shown to be on the order of 0.5 percent, in high ratio flow splits and flow variations of 2:1. For maintaining accuracy in the flow split, a differential pressure regulator 20 is disposed downstream of the channeled plugs in conjunction with a variable valve 22 disposed in the sample stream 14 for regulation of flow therethrough.

Figure 2:
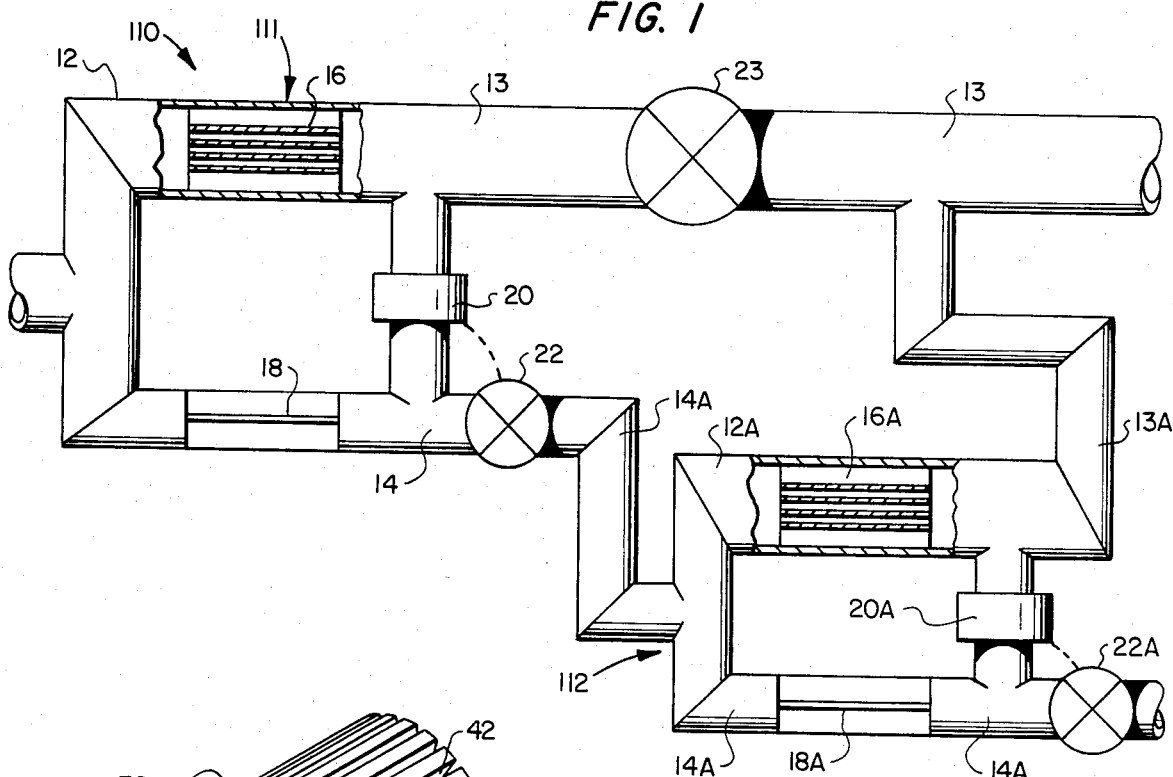
FIG. 2 is an alternative embodiment of the flow sampler of FIG. 1 provided in a two-stage arrangement for larger splits.

Referring now to FIG. 2, there is shown one embodiment of a two stage system 110 for determination of energy flow in a pipeline 12. The system 110 includes a first stage 111 comprising channeled flow splitter 16 and channeled plug 18 disposed within a flow system of the type illustrated in FIG. 1. Downstream of valve 22, however, a second stage flow splitting and sampling system is provided. Conduit 14A vectors flow from sample line 14 into a second stage flow splitting and sampling network 112. Parallel flow paths 12A and 14A further split the flow from sample line 14 and return a substantial portion thereof back to line 13 through return line 13A. An adjustable valve 23 may be provided in line 13 for manually or automatically reducing the downstream pressure to facilitate flow re-entry. The second stage flow division is also preferably provided by the channeled plug configuration set forth and described herein. The flow egressing from plug or capillary 18A is thus a substantially higher split than previously possible because the sample issuing from the first stage flow split is proportionally split again into yet a smaller sample in accordance with the present invention. A differential pressure regulator 20A disposed downstream of the channeled plugs 16A and 18A preferably actuates variable valve 22A disposed in the sample stream 14A for second stage flow regulation. It may thus be seen that multiple flow splitting stages are possible for higher split ratios in accordance with the principles of the present invention.

Figure 3:
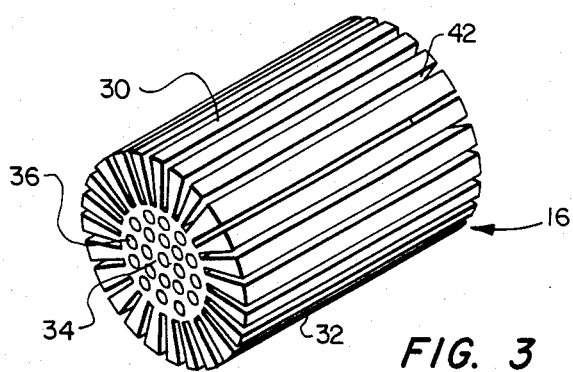
FIG. 3 is a perspective view of a channeled plug assembly constructed in accordance with the present invention and of the type shown installed in the main gas flow line in FIG. 1.

Referring now to FIG. 3, there is shown a perspective view of one embodiment of the channeled plug 16 of the present invention. The plug 16 includes a generally cylindrical body portion 30 which, in the present embodiment, includes a plurality of generally rectangular slots 32 formed in the sides thereof. As will be discussed below, a plurality of channel configurations may be utilized within certain hydraulic diameter constraints.

The slots 32 of FIG. 3 extend radially inwardly toward the center 34 of the body 30 where a plurality of circular apertures 36 are formed therethrough. The slotted channels 32 are preferable to the conventional circular apertures of the type found in the prior art because such a slot configuration adds more flow area for the same hydraulic diameter. In this manner, a channeled plug 18 in the sample line, having the same hydraulic diameter but smaller flow area compared to the plug 16, can be used in conjunction with said plug 16 to produce a substantially higher split ratio than conventionally available. Moreover, a substantially greater channel flow area may be provided in the plug body 30 in this configuration. Such a method and apparatus further reduces instrument maintenance by providing a flow splitter having no moving parts and much higher proportionality accuracy than conventional flow splitter.

Flow sampling systems of the type described above require, by definition, constant flow ratios for purposes of accuracy. To assure a constant flow ratio, the flow impedance across the main plug 16 and sample plug 18 must be equal. This requirement is met by placing plugs having channels formed therein in the main line 12 and in the sample line 14. The channels 32 in the plug body 30 have relatively equivalent lengths and hydraulic diameters. The channels in the sample line plug 18 have relatively equivalent hydraulic diameters which are on the same order of magnitude as the average hydraulic diameter of the channels 32 of the main plug 16. In addition, the pressure drop across the plugs 16 and 18 is preferably held constant by the pressure regulator 20. These constraints then impose equal flow impedances across these flow elements. A critical consideration is, however, the channel configuration within the plugs 16 and 18 and the utilization of relatively equivalent hydraulic diameters as described above.

The definition of hydraulic diameter may be simply stated as four times the cross-sectional area divided by the wetted perimeter of the channel. The following formula 38 thus defines the hydraulic diameter of a circular hole:

$$D_H = 4(\pi D^2/4)/(\pi D) = D \quad (38)$$

The formula for the hydraulic diameter of a rectangular channel, or slot, is given by formula 39 as follows:

$$D_H = 4lw/(2l+2w) = 2lw/(l+w) \quad (39)$$

the above being true where:
$D_H$ = hydraulic diameter
D = diameter of aperture
l = length of slot
w = width of slot The equation for pressure drop across a channeled plug is next given by the equation:

$$PC = fLG^2/2dRg \quad (40)$$

where
PC = pressure change
f = Fanning Friction Factor
L = length of pipe
G = mass flux of gas
g = acceleration due to gravity
d = density (average)
R = hydraulic radius It may thus be seen that a sample line plug having a channel formed therein with a circular aperture of a relatively small diameter and a relatively small area for flow may reflect the same hydraulic diameter relative to flow impedance as a substantially larger channel in the main plug 16 which has a different shape. This corresponding area relationship and shape differential may best be seen by referring again to FIG. 3 wherein there is shown plug 30 with a plurality of slots 42 adjacent apertures 36 having relatively equivalent hydraulic diameters. Therefore, a channeled plug such as a capillary 18 disposed in sample line 14 having a diameter on the same order of magnitude as hole 36 will be effective in providing proportional flow sampling. In this manner, a much larger average flow area can be presented in main plug 16 per channel than in the average channel of capillary 18. Such a condition permits a gross change in main line flow rates without adversely effecting the proportionality of the flow and the accuracy of the sample.

Still referring to FIG. 3, the rectangular slots 42 may be fabricated in the cylindrical body sections 30 much quicker and more efficiently than cylindrical apertures from a production and quality control standpoint. This is a marked advantage over prior art flow dividers utilizing simple aperture arrays. Moreover, it is necessary to provide channels within the main plug 16 which have a greater average cross-sectional area than the channels within the sample line plug 18 for corresponding hydraulic diameters within the same order of magnitude. A myriad of channel cross-sectional configurations are thus possible, such as diamond, square, and similar geometric shapes (not shown). What is shown is a representative array of radially aligned rectangular slots as defined below.

By way of example only, the plug 16 illustrated in FIG. 3, having a radius of 1 and ⅛ inch, slot widths (w) of 1/16 inch and slot lengths (l) of 7/16 inch will provide a split of 79 to 1 over any flow range when used with a 7/64 inch diameter, cylindrical shaped channel capillary 18. The circular apertures 36 of the plug 30 are, therefore, by definition 7/64 inches in diameter. The length of the plug 30 is preferably as long as possible but at least one inch. The average hydraulic diameter for such channels in the plugs would be 0.109 with measurements made as set forth above and Reynolds number above 2,000. The flow split with such plug configurations has been shown to vary less than plus or minus 0.45 percent over a flow range of 2 to 1 and less than plus or minus 0.7 percent over a flow range of 5 to 1.

It is thus believed that the operation and construction of the present invention will be apparent from the foregoing description. While the method and apparatus shown and described has been characterized as being preferred it will be obvious that various changes and modifications may be made therein without departing from the spirit and scope of the invention as defined in the following claims.

We claim:

1. Apparatus for taking a proportionally constant flowing sample from a gas stream flowing through a main gas flow line comprising:
    a first channeled plug flow splitter mounted within said main gas line and being formed with a plurality of channels extending therethrough having relatively equivalent hydraulic diameters;
    a sample line extending out of said main gas line upstream of said first plug for receiving a select flow of gas therefrom;
    a second channeled plug mounted within said sample line and having at least one channel formed therein for the passage of gas therethrough having an hydraulic diameter within the same order of magnitude as the hydraulic diameter of said channels of said first channeled plug; and
    said channels of said first plug being formed with an average cross-sectional area substantially greater than the cross-sectional area of said channel of said second plug.

2. The apparatus as set forth in claim 1 wherein said hydraulic diameters of each of said channels of said first plug are within ten percent of one another.

3. The apparatus as set forth in claim 1 wherein said order of magnitude of said channels comprises a ten to one ratio.

4. The apparatus as set forth in claim 1 and further including:
    means for detecting the magnitude of pressure drop across said first and second plugs; and
    means for altering the pressure and flow conditions across said plugs to thereby establish flow through said sample line at a constant proportion of the flow through said main gas flow line.

5. The apparatus as set forth in claim 1 wherein said channels of said first plug are constructed in a generally rectangular slotted configuration.

6. The apparatus as set forth in claim 5 wherein said rectangular slots of said plug are formed in a radially extending pattern through said plug.

7. The apparatus as set forth in claim 6 wherein said first plug further includes a plurality of cylindrical channels formed in an array disposed radially inwardly of said slots.

8. The apparatus as set forth in claim 7 wherein said channel of said second plug is cylindrical, having a diameter substantially equal to twice the value of the product of said first plug slot length times slot width divided by the sum of said slot length and slot width.

9. The apparatus as set forth in claim 1 wherein a second stage flow splitting and sampling system is provided downstream of said sample line for receiving flow therefrom and providing a secondary flow split.

10. The apparatus as set forth in claim 9 wherein said second stage flow splitting system comprises:
    first and second flow lines coupled in parallel flow relationship to said sample line;
    a third channeled plug flow splitter mounted within said first flow line and being formed with a plurality of channels extending therethrough having relatively equivalent hydraulic diameters;
    a fourth channeled plug mounted within said sample line and having at least one channel formed therein for the passage of gas therethrough having an hydraulic diameter within the same order of magnitude as the hydraulic diameter of said channels of said third channeled plug; and
    said channels of said third plug being formed with an average cross-sectional area substantially greater than the cross-sectional area of said channel of said fourth plug.

11. The apparatus as set forth in claim 10 and including means for detecting the magnitude of the pressure drop across said third and fourth plugs and means for altering the pressure and flow conditions across said fourth plug to selectively match those obtained across said third plug to thereby establish flow through said second flow line at a constant proportion of the flow through said first flow line.

12. A method of taking a flowing sample of gas flowing through a line, which flowing sample is constantly proportionate to the flow rate of said flowing gas, said method comprising:
    providing a first channeled plug flow splitter mounted within said line and being formed with a plurality of channels extending therethrough having relatively equivalent hydraulic diameters;
    passing said gas flowing through said line through said first plug;
    drawing a flowing sample of said gas from said line at a point upstream of said first plug into a sample line;
    providing a second channeled plug mounted within said sample line having at least one channel formed therein for the passage of gas therethrough having an hydraulic diameter within the same order of magnitude as the hydraulic diameter of said channels of said first channel plug, wherein said channels of said first plug are formed with an average corss-sectional area substantially greater than the cross-sectional area of said channels of said second plug; and
    passing said flowing sample of said gas in said sample line through said second channel plug mounted in said sample line.

13. The method as set forth in claim 12 and further including the step of equalizing the pressure downstream of said first and second plugs.

14. The method as set forth in claim 13 wherein said step of equalizing said downstream pressure includes detecting the difference between said pressures and operating a valve in said sample line in a direction to eliminate said difference.

15. The method as set forth in claim 12 and further including the step of providing said first plug with channels having hydraulic diameters within ten percent of one another.

16. The method as set forth in claim 12 and further including providing said first plug with generally rectangular channels and said second plug with at least one generally cylindrical channel.

17. The method as set forth in claim 16 and including providing said cylindrical channels with a diameter substantially equal to twice the value of the product of said first plug rectangular channel length times channel width divided by the sum of said length and width.

* * * * *